United States Patent [19]

Weitz et al.

[11] 4,064,124

[45] Dec. 20, 1977

[54] MANUFACTURE OF PYRAZINES

[75] Inventors: Hans-Martin Weitz, Frankenthal; Rolf Fischer, Heidelberg, both of Germany

[73] Assignee: BASF Aktiengesellschaft, Ludwigshafen, Germany

[21] Appl. No.: 572,136

[22] Filed: Apr. 28, 1975

[51] Int. Cl.² .................... C07D 241/04; C07D 241/06
[52] U.S. Cl. .......................... 260/250 B; 260/250 BC; 260/348.45
[58] Field of Search ...................... 260/250 BC, 250 B

[56] References Cited

U.S. PATENT DOCUMENTS

| 3,637,764 | 1/1972 | Newman et al. | 260/348 |
|---|---|---|---|
| 3,814,757 | 6/1974 | Donald | 260/250 R |
| 3,881,025 | 4/1975 | Flament | 260/250 R |
| 3,925,378 | 12/1975 | Voges et al. | 260/250 B |
| 3,928,351 | 12/1975 | Donald | 260/250 BN |
| 3,948,895 | 4/1976 | Donald | 260/250 BN |

FOREIGN PATENT DOCUMENTS

| 1,382,468 | 1/1975 | United Kingdom | 260/250 |
|---|---|---|---|
| 1,383,082 | 0000 | United Kingdom | 250/ |
| 1,383,083 | 0000 | United Kingdom | 260/306.7 R |
| 1,383,084 | 0000 | United Kingdom | 260/250 |
| 1,420,057 | 0000 | United Kingdom | 260/250 B |

OTHER PUBLICATIONS

Newman et al. Chemical Abstracts vol. 76, 113046g (1972).

Primary Examiner—Donald G. Deus
Assistant Examiner—Jose Tovar
Attorney, Agent, or Firm—Keil, Thompson & Shurtleff

[57] ABSTRACT

Pyrazines are manufactured by reaction of nitrooxiranes with ammonia. The products are starting materials for the manufacture of dyes, fungicides and pharmaceuticals.

7 Claims, No Drawings

MANUFACTURE OF PYRAZINES

The present invention relates to a process for the manufacture of pyrazines by reaction of nitrooxiranes with ammonia.

It is known that 2,5-disubstituted and 2,3,5,6-tetrasubstituted pyrazines may be manufactured by condensing two molecules of an α-aminoketone. The dihydropyrazines first formed can be dehydrogenated by oxidizing agents, e.g. hydrogen peroxide or mercury salts. In another process, α-hydroxyketones are heated with ammonium acetate (Bull. Soc. Chim. France (1965), 3476 – 3478).

The syntheses of substituted pyrazines suffer from the disadvantage that α-hydroxyketones and, above all, α-aminoketones cannot be manufactured simply and in good yield, especially on an industrial scale.

Houben-Weyl, Methoden der Organischen Chemie, Volume 11/1, page 311 discloses that ammonia reacts with ethylene oxide, even if the former is present in excess, to give a mixture of β-aminoethyl alcohol, diethanolamine and triethanolamine. It is pointed out that it is impossible to control the reaction so as to produce one of the bases only. At the same time, some of the ethylene oxide can react further to form hydroxyethyl ethers.

It is an object of the present invention to provide a new, simpler and more economical process for the manufacture of a large number of pyrazines in better yield and higher purity, particularly on an industrial scale.

We have found that pyrazines of the formula

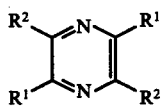

wherein the $R^1$'s and $R^2$'s may be identical or different and each is hydrogen or an aliphatic, cycloaliphatic, araliphatic or aromatic radical and furthermore each $R^1$ and the adjacent $R^2$ together with the two carbon atoms joining the two radicals may be members of an alicyclic ring, are obtained advantageously by reacting nitrooxiranes of the formula II

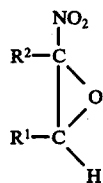

wherein $R^1$ and $R^2$ have the above meanings, with ammonia.

Where 2-nitro-2,3-diphenyl-oxirane is used, the reaction may be represented by the following equation:

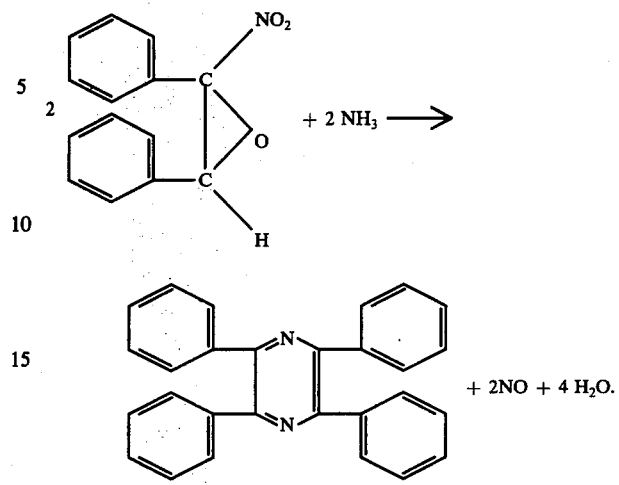

In comparison to the conventional processes, the process of the invention surprisingly can be used to produce a large number of pyrazines more simply and more economically, and in better yield and higher purity, even on an industrial scale. The starting materials are readily obtainable and may be manufactured simply and in high yield, e.g. from corresponding nitroolefins by reaction with aqueous hydrogen peroxide, of from 10 to 30 percent strength by weight, and dilute sodium hydroxide solution in polar solvents such as water, methanol, dioxane and diethyl ether, e.g. in accordance with the process described in Zh. Org. Khim., 8 (1972), 2325 – 2327 (English Edition, pages 2371 to 2373). A further advantage is that the reaction mixture obtained by reaction of the nitrooxiranes with ammonia is simple to work up. No significant formation of a mixture of heterogeneous by-products such as monoalkanol, dialkanol and trialkanol derivatives of ammonia and hydroxyethyl ethers is observable. In the light of the state of the art, all these advantageous results shown by the process are surprising.

The starting material II is reacted with ammonia in the stoichiometric amount or in excess, preferably in a ratio of from 5 to 50 moles of ammonia per mole of starting material II. Preferred starting materials II and, accordingly, preferred end products I are those wherein the $R^1$'s and $R^2$'s may be identical or different and each is alkyl of 1 to 10, preferably of 1 to 4, carbon atoms, cyclopentyl, cyclohexyl, aralkyl of 7 to 12 carbon atoms, phenyl, naphthyl or hydrogen and furthermore each $R^1$ and the adjacent $R^2$ together with the two adjacent carbon atoms may be members of an alicyclic ring of from 5 to 12, especially of 5 or 6, members. The above radicals and rings can in addition be substituted by groups and/or atoms which are inert under the reaction conditions, e.g. alkyl or alkoxy or 1 to 4 carbon atoms, or nitro.

Examples of suitable nitrooxiranes II are: 2-nitro-2-methyl-oxirane, 2-nitro-2-phenyl-oxirane, 3-nitro-3-methyl-2-cyclohexyl-oxirane, 3-nitro-3-methyl-2-phenyl-oxirane, 3-nitro-3-ethyl-2-phenyl-oxirane, 3-nitro-3-ethyl-2-[p-methoxyphenyl]-oxirane, 2-nitro-2,3-diphenyl-oxirane, 2-nitro-2,3-dimethyl-oxirane, 2-nitro-2,3-tetramethyleno-oxirane, 2-nitro-2,3-hexamethyleno-oxirane, 2-nitro-2,3-decamethyleno-oxirane, 2-nitro-2,3-trimethyleno-oxirane, 3-nitro-2-benzyl-oxirane, 3-nitro-2-p-nitro-phenyl-oxirane, 3-nitro-2-cyclopentyl-oxirane, 2-nitro-2-decyl-oxirane, 2-nitro-2-n-propyl-oxirane and 2-nitro-2-n-butyl-oxirane.

The nitroolefins 1,2-disubstituted by aromatic and/or aliphatic radicals, which are required for the manufacture of the starting materials II, may be obtained by reaction of unsubstituted or substituted aromatic aldehydes with nitroalkanes, nitroolefins with aliphatic substituents may be manufactured by dehydration of the corresponding nitro alcohols and cycloaliphatic nitroolefins may be manufactured by reaction of cycloalkenes with dinitrogen tetroxide in the presence of bases.

The reaction is in general carried out at from 20° to 200° C, preferably from 40° to 100° C, under atmospheric or superatmospheric pressure, preferably at from 10 to 100 atmospheres, and continuously or batchwise. If necessary, solvents which are inert under the reaction conditions are used to dissolve or suspend the starting mixture and reaction mixture. It is advantageous to use organic solvents which are immiscible or sparingly miscible with water and boil at above 100° C under normal pressure or under pressures of up to 10 atmospheres, the preferred boiling points being from 60° to 190° C under normal pressure. Suitable solvents are aromatic hydrogcarbons, e.g. benzene, toluene, ethylbenzene, o-, m- and p-xylene and isopropylbenzene; halohydrocarbons, especially chlorohydrocarbons, e.g. tetrachloroethylene, 1,2-dichloropropane, tetrachloroethane, carbon tetrachloride, chloroform, trichloroethane, trichloroethylene, pentachloroethane, cisdichloroethylene, 1,2-dichloroethane, methylene chloride, 1,1-dichloroethane, 1,2-dichloroethane, 1,2-cis-dichloroethylene, n-butyl chloride and 2-, 3- and iso-butyl chloride, and appropriate mixtures. The solvent is suitably used in amounts of from 5 to 1,000% by weight, preferably from 5 to 50% by weight, based on the starting material II. Ammonia may be used in the form of an aqueous solution, in general of from 25 to 35 percent strength by weight, or as a solution in an organic solvent, e.g. one of those mentioned above, or advantageously, in the liquid form.

The reaction may be carried out as follows. A mixture of the starting materials and, where appropriate, of the solvent is kept at the reaction temperature for from 5 to 10 hours. The end product is then isolated from the mixture by conventional methods, e.g. by evaporation of the residual ammonia, extraction with a suitable solvent, e.g. diethyl ether, and distillation of the extract, or filtration.

The end products I which may be manufactured by the above process are valuable starting materials for the manufacture of dyes, fungicides and pharmaceuticals. The pyrazines with aliphatic substituents are flavoring agents, or additives to improve the smell and taste of foodstuffs, beverages and tobacco. On oxidation with e.g., potassium permanganate they give pyrazine carboxylic acids which in turn give, e.g. by reaction with ammonia, cyanopyrazines which are curing agents for epoxy resins and starting materials for the manufacture of diuretics. Dicyanopyrazines and tricyanopyrazines are used as phosphors. Certain pyrazinecarboxylic acid amides are hypotensives and agents for assisting the sugar metabolism. With regard to uses, reference may be made to German Published Applications 2,140,649 and 2,216,925, Japanese Application 40,065/72 and Netherlands Pat. No. 72/03,057.

In the Examples which follow, parts are by weight and bear the same relation to parts by volume as that of the kilogram to the liter.

EXAMPLE 1 a. 2-Nitro-2,3-hexamethyleno-oxirane

In a stirred vessel, 31 parts by volume of 2 N sodium hydroxide solution are added to a mixture of 200 parts by volume of methanol, 41 parts by volume of 15 percent strength by weight aqueous hydrogen peroxide and 18.5 parts of 1-nitro-cyclooctene-(1) ($N_D^{20}$ = 1.5100) at from 0° to 4° C, whilst cooling. 300 parts by volume of ice water are added to the mixture at 20° C. The reaction mixture is then stirred further for 30 minutes at room temperature after which the precipitate is filtered off. After drying, 16.3 parts of 2-nitro-2,3-hexamethyleno-oxirane (80% of theory), melting at from 35° to 36° C after recrystallization from methanol are obtained. Boiling point at 0.1 mm Hg = 64° C.

b. 2,3,5,6-Bis-hexamethylenopyrazine 14.5 parts of 2-nitro-2,3-hexamethyleno-oxirane and 100 parts by volume of liquid ammonia are shaken for 6 hours in an autoclave, at 50° C and 25 atmospheres. The solid residue left after evaporation of the ammonia in the autoclave is mixed with 100 parts by volume of water. The aqueous suspension is extracted with three times 50 parts by volume of diethyl ether, the combined ether extracts are dried and the ether is evaporated off. 9.8 parts of 2,3,5,6-bis-hexamethyleno-pyrazine (94% of theory) melting at from 115° to 116° C after recrystallization from acetone are obtained.

EXAMPLE 2

2,3,5,6-Tetraphenylpyrazine 12 parts of 2-nitro-2,3-diphenyl-oxirane melting at from 109° to 110° C and 100 parts by volume of liquid ammonia are shaken for 6 hours in an autoclave at 100° and 65 atmospheres. After evaporation of the ammonia, the solid residue is treated with water and the constituent left undissolved is filtered off and recrystallized from glacial acetic acid. 5.2 parts of 2,3,5,6-tetraphenylpyrazine (54% of theory) melting at from 253° to 254° C are obtained.

EXAMPLE 3

2,5-Diethyl-3,6-diphenylpyrazine 10 parts of 3-nitro-3-ethyl-2-phenyl-oxirane (boiling point at 2 mm Hg = from 100° to 103° C) and 100 parts by volume of liquid ammonia are shaken for 6 hours in an autoclave at 50° C and 22 atmospheres; the mixture is then worked up analogously to Example 1b). 5.4 parts of 2,5-diethyl-3,6-diphenylpyrazine (72% of theory) melting at from 145° to 146° C after recrystallization from methanol are obtained.

EXAMPLE 4

2,5-Dimethyl-3,6-diphenylpyrazine 9 parts of 3-nitro-3-methyl-2-phenyl-oxirane (boiling point at 0.5 mm Hg = from 95° to 97° C) and 90 parts by volume of liquid ammonia are shaken for 6 hours in an autoclave at 60° C and 28 atmospheres. The mixture is then worked up analogously to Example 1b). 2.9 parts of 2,5-dimethyl-3,6-diphenylpyrazine (44% of theory) melting at from 126° to 127° C after recrystallization from ethanol are obtained.

We claim:

1. A process for the manufacture of pyrazines of the formula

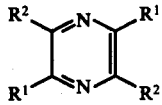

I wherein the R¹'s and R²'s may be identical or different and each is hydrogen or an alkyl of 1 to 10 carbon atoms, cyclopentyl, cyclohexyl, aralkyl of 7 to 12 carbon atoms, phenyl, naphthyl and furthermore each R¹ and the adjacent R² together with the two carbon atoms joining the two radicals may be members of an alicyclic ring of from 5 to 12 members, wherein the above radicals and rings can in addition be substituted by alkyl or alkoxy of 1 to 4 carbon atoms or nitro in which nitrooxiranes of the formula

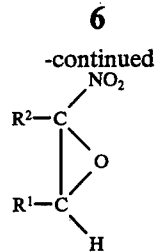

II wherein R¹ and R² have the above meanings, are reacted with ammonia.

2. A process as set forth in claim 1, wherein the reaction is carried out with from 5 to 50 moles of ammonia per mole of starting material II.

3. A process as set forth in claim 1, wherein the reaction is carried out at from 20° to 200° C.

4. A process as set forth in claim 1, wherein the reaction is carried out at from 40° to 100° C.

5. A process as set forth in claim 1, wherein the reaction is carried out under a pressure of from 10 to 100 atmospheres.

6. A process as set forth in claim 1, wherein the reaction is carried out with from 5 to 1,000% by weight, based on starting material II, of a solvent which is inert under the reaction conditions.

7. A process as set forth in claim 1, wherein the reaction is carried out with a solvent which is inert under the reaction conditions and boils at above 100° C under normal pressure or under pressures of up to 10 atmospheres.

* * * * *

UNITED STATES PATENT AND TRADEMARK OFFICE
CERTIFICATE OF CORRECTION

PATENT NO. : 4,064,124
DATED : December 20, 1977
INVENTOR(S) : WEITZ ET AL

It is certified that error appears in the above-identified patent and that said Letters Patent are hereby corrected as shown below:

In the heading, insert after "[22] Filed: Apr. 28, 1975" the following:

-- [30]  Foreign Application Priority Data

May 25, 1974   Germany . . . . . 2425355--.

Signed and Sealed this

Twenty-fourth Day of April 1979

[SEAL]

Attest:

RUTH C. MASON
Attesting Officer

DONALD W. BANNER
Commissioner of Patents and Trademarks